(12) United States Patent
Gordon et al.

(10) Patent No.: US 10,548,636 B2
(45) Date of Patent: Feb. 4, 2020

(54) FORCE ADJUSTABLE SPRING DISTRACTOR

(71) Applicants: Christopher B. Gordon, Cincinnati, OH (US); Thomas S. Johnston, Jr., Jacksonville, FL (US); Michael Mantia, Jacksonville, FL (US)

(72) Inventors: Christopher B. Gordon, Cincinnati, OH (US); Thomas S. Johnston, Jr., Jacksonville, FL (US); Michael Mantia, Jacksonville, FL (US)

( * ) Notice: Subject to any disclaimer, the term of this patent is extended or adjusted under 35 U.S.C. 154(b) by 181 days.

(21) Appl. No.: 15/723,940

(22) Filed: Oct. 3, 2017

(65) Prior Publication Data

US 2018/0092663 A1    Apr. 5, 2018

Related U.S. Application Data

(60) Provisional application No. 62/403,404, filed on Oct. 3, 2016.

(51) Int. Cl.
| | | |
|---|---|---|
| *A61B 17/66* | (2006.01) | |
| *A61B 17/80* | (2006.01) | |
| *A61B 17/00* | (2006.01) | |

(52) U.S. Cl.
CPC .......... *A61B 17/66* (2013.01); *A61B 17/8019* (2013.01); *A61B 17/8061* (2013.01); *A61B 17/663* (2013.01); *A61B 2017/00862* (2013.01)

(58) Field of Classification Search
CPC .............. A61B 17/645; A61B 17/6466; A61B 17/6433; A61B 2017/606; A61B 17/66; A61B 17/681; Y10T 403/29; F16G 11/12

USPC ............................................ 606/57, 58, 105
See application file for complete search history.

(56) References Cited

U.S. PATENT DOCUMENTS

| | | | | |
|---|---|---|---|---|
| 3,610,606 | A * | 10/1971 | Andrews | F16F 15/02 267/74 |
| 3,751,083 | A * | 8/1973 | Jacobson | F16B 7/06 403/46 |
| 4,011,979 | A * | 3/1977 | Hagen | B23K 37/053 228/49.3 |
| 5,377,556 | A * | 1/1995 | Byrnes | F16G 11/12 74/500.5 |
| 5,466,083 | A * | 11/1995 | Hogg | A01B 59/004 403/43 |
| 5,672,175 | A * | 9/1997 | Martin | A61B 17/025 606/105 |
| 5,702,196 | A * | 12/1997 | Petercsak | F16B 7/06 280/93.502 |
| 5,902,304 | A * | 5/1999 | Walker | A61B 17/663 606/282 |

(Continued)

*Primary Examiner* — David W Bates
(74) *Attorney, Agent, or Firm* — Thomas C. Saitta

(57) ABSTRACT

A force adjustable spring distractor device having an elongated, relatively thin guide plate, a force adjusting rod member having first and second oppositely threaded portions, first and second anchor bodies mounted on the guide plate and the threaded portions of the rod, first and second distractor bodies mounted on the guide plate and the rod, and first and second distraction springs connecting the anchor bodies to the distractor bodies, whereby rotation of the force adjusting rod results in separation of the anchor bodies and elongation of the distraction springs, thereby imparting a separation force to the distractor bodies.

20 Claims, 3 Drawing Sheets

(56) References Cited

U.S. PATENT DOCUMENTS

| | | | | |
|---|---|---|---|---|
| 6,355,036 B1* | 3/2002 | Nakajima | A61B 17/66 | 606/54 |
| 6,491,646 B1* | 12/2002 | Blackledge | A61M 25/0905 | 600/585 |
| 6,786,910 B2* | 9/2004 | Cohen | A61B 17/66 | 606/71 |
| 7,451,962 B1* | 11/2008 | Kennedy | F16B 7/06 | 254/231 |
| 7,588,579 B2* | 9/2009 | Mommaerts | A61B 17/663 | 606/105 |
| 7,998,216 B2* | 8/2011 | Elsalanty | A61B 17/8004 | 606/282 |
| 8,808,290 B2* | 8/2014 | Dubois | A61B 17/663 | 606/58 |
| 9,289,252 B2* | 3/2016 | Dacosta | A61B 17/808 | |
| 9,700,353 B2* | 7/2017 | Harris | A61B 17/66 | |
| 9,872,706 B1* | 1/2018 | Mullaney | A61B 17/6475 | |
| 2005/0010233 A1* | 1/2005 | Wittenstein | A61B 17/7216 | 606/90 |
| 2005/0191118 A1* | 9/2005 | Kay | B60P 7/0838 | 403/48 |
| 2005/0203509 A1* | 9/2005 | Chinnaian | A61B 17/6491 | 606/54 |
| 2005/0246034 A1* | 11/2005 | Soubeiran | A61B 17/7216 | 623/23.45 |
| 2006/0058798 A1* | 3/2006 | Roman | A61B 17/8004 | 606/71 |
| 2006/0280549 A1* | 12/2006 | Hsieh | B63B 25/28 | 403/43 |
| 2008/0039861 A1* | 2/2008 | Ahmad | A61B 17/1637 | 606/105 |
| 2009/0054897 A1* | 2/2009 | Gordon | A61B 17/663 | 606/57 |
| 2009/0198234 A1* | 8/2009 | Knuchel | A61B 17/62 | 606/57 |
| 2011/0253956 A1* | 10/2011 | Smetz | F16G 3/006 | 254/100 |
| 2013/0338712 A1* | 12/2013 | Massenzio | A61B 17/7014 | 606/252 |
| 2014/0025075 A1* | 1/2014 | Hokanson | A61B 17/66 | 606/58 |
| 2014/0128868 A1* | 5/2014 | Harrison | A61B 17/7016 | 606/60 |
| 2014/0336648 A1* | 11/2014 | Van Aaken | A61B 17/66 | 606/58 |
| 2016/0058485 A1* | 3/2016 | Staehler | A61B 17/8004 | 606/282 |
| 2016/0265623 A1* | 9/2016 | Kingery | F16G 11/12 | |
| 2018/0296246 A1* | 10/2018 | Perret | A61B 17/6425 | |
| 2018/0344354 A1* | 12/2018 | Mullaney | A61B 17/62 | |
| 2019/0031079 A1* | 1/2019 | Robins | B60P 7/083 | |
| 2019/0269438 A1* | 9/2019 | Simpson | A61B 17/7017 | |

* cited by examiner

FORCE ADJUSTABLE SPRING DISTRACTOR

BACKGROUND OF THE INVENTION

This application relates generally to the field of medical devices known as bone distractors, devices that continuously or incrementally separate two bone segments. More particularly, this application relates to such devices that utilize tensioned members to provide the distraction force.

In some bone distraction procedures it is desirable to provide a continuously applied separation force rather than an incrementally applied separation force. It is also often desirable to provide a distraction device in which the distraction force is adjustable. A distraction device having both of these characteristics is particularly desirable for the correction of craniosynostosis, a condition that occurs in infants as the brain develops and grows in size. The skull bones of an infant are initially joined together by fibrous tissue, known as sutures, which extend as the brain grows and later ossify once brain growth decreases. In craniosynostosis the sutures ossify too soon, with the premature fusion resulting in skull deformities that, beyond aesthetics, may adversely affect eyesight or breathing, or may even be life threatening.

To address this condition, surgery is performed to separate the prematurely fused cranial bones to allow for expansion. However, it is necessary to continuously distract the bone portions to prevent re-fusion before the desired final size and shape of the cranium is reached.

It is an object of this invention to provide a distraction device that is especially suitable for use in the treatment of craniosynostosis, wherein the distractor provides a continuous distraction force and is force adjustable, both initially and during the treatment process.

DETAILED DESCRIPTION OF THE INVENTION

Figure 1:
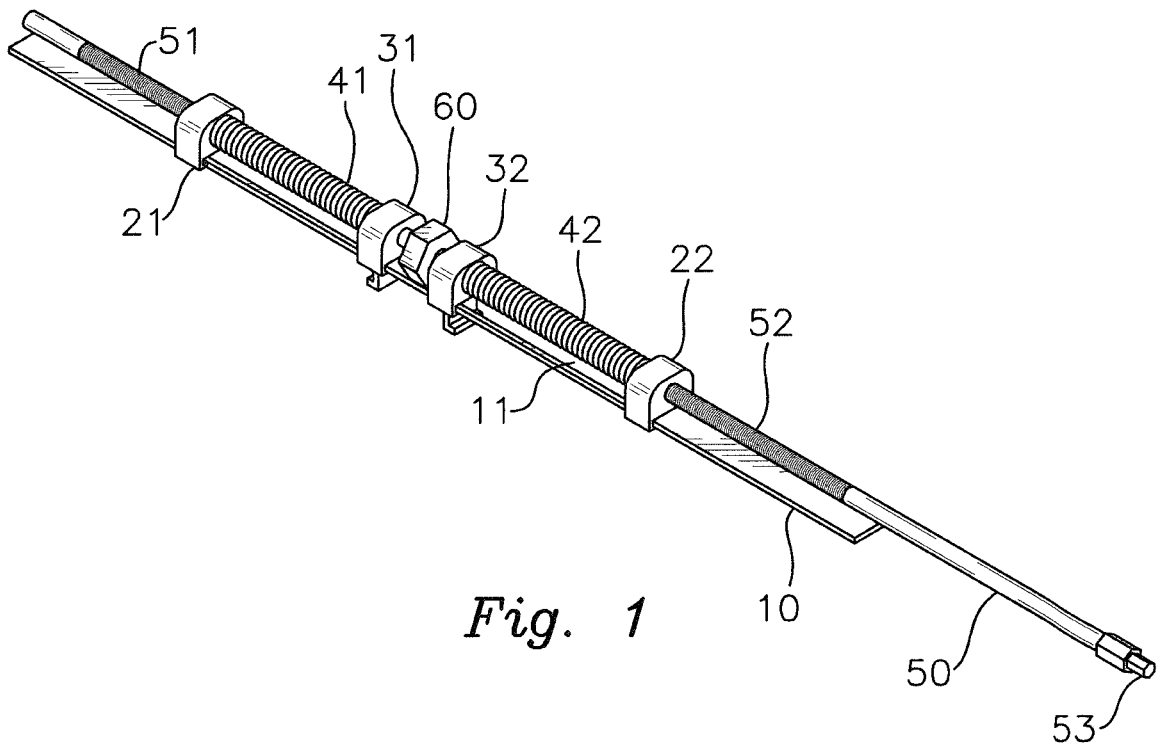
FIG. 1 is perspective view of an embodiment of the distractor shown in the pre-adjustment, non-tensioned state.

In general, the invention is a force adjustable spring distractor device that is particularly suitable for use in the treatment of craniosynostosis, the distractor having a tensioning or biasing mechanism to adjust the separation force imparted by the spring members both initially and during the treatment process. To address craniosynostosis, a surgeon performs a craniotomy to create an opening or slot between adjacent cranial bones that need to be distracted due to premature fusion. The force adjustable spring distractor device is then used to apply distracting force to the adjacent cranial bones. Although the invention is discussed herein primarily with regard to the treatment of craniosynostosis, it is to be understood that the distractor may be utilized with other types of bones when a force adjustable distraction is needed. Furthermore, the drawings are provided as illustrative disclosure and are not intended to be limiting as to the scope of the invention. The terms axial, coaxial or the like as used herein shall refer to the direction defined by the central axis of the elongated force adjusting rod member.

The distractor device comprises in general an elongated, relatively thin, guide plate 10, a first anchor body or member 21, a second anchor body or member 22, a first distractor body or member 31, a second distractor body or member 32, a first distraction spring 41, a second distraction spring 42, and an externally threaded force adjusting rod member 50. The force adjusting rod member 50 defines the axial or elongation direction of the distractor device.

The guide plate 10 is composed of a rigid material, or a malleable material possessing sufficient strength for its intended use once shaped to the desired configuration, such as a metal. In the embodiment shown, the guide plate 10 is provided with a centrally located elongated opening or guide slot or slots 11 that guides the distractor bodies 31/32 in the axial direction and limits movement of the distractor bodies 31/32 in non-axial directions. The distractor bodies 31/32 are bone contacting members that are disposed within the craniotomy opening or slot created by a surgeon, such that the first distractor body 31 abuts a first cranial bone member on a first side of the craniotomy and the second distractor abuts a second cranial bone member on the second or opposing side of the craniotomy, in a manner whereby separation of the first distractor body 31 from the second distractor body 32 applies distracting separation force against the opposing bone members to prevent undesired fusion of the cranial bones.

In the embodiment shown, each of the distractor bodies 31/32 comprises a bone abutting member 33 preferably formed in the shape of a hook having a depending leg portion 35 and a foot portion 36, the foot portion 36 adapted and structured to be positioned beneath the cranial bones to better retain the distraction device in the proper position and apply distractive force relative to the cranial bones. Other shapes for the bone abutting member 33 may be utilized to provide force against the cranial bones, and it is also possible to structure the distractor bodies 31/32 with a bone plate member that is adapted and structured to be mechanically fastened by bone screws or otherwise bonded to the cranial bones. The first and second distractor bodies 31/32 each possess a bore 34 that is sized to receive the force adjusting rod 50 therethrough, the distractor bodies 31/32 being free sliding relative to the force adjustable rod 50 along the axial direction, i.e., the distractor bodies 31/32 do not mechanically engage the threading of the force adjusting rod 50. The distractor bodies 31/32 are also free sliding relative to the guide plate 10 in the elongated axial direction, i.e., the distractor bodies 31/32, although limited in non-axial movement due to abutment with the guide plate 10 or the guide slot 11, do not mechanically engage the guide plate 10. In the embodiment shown, the leg portion 35 of the bone abutting member 33 extends through the guide slot 11, the sides of the guide plate 10 preventing movement perpendicular to the elongated direction.

In the embodiment shown, the first and second anchor bodies 21/22 are positioned outwardly from the first and second distractor bodies 31/32, respectively, along the guide plate 10 and along the force adjusting rod member 50. Each anchor body 21/22 preferably comprises a mounting slot 23 adapted for mating connection to the guide plate 10, the mounting slot 23 having shoulders or rails 24 that allow for free sliding movement of the anchor bodies 21/22 along the guide plate 10 in the elongation direction. Alternatively, the mounting slot 23 may be enclosed so as to fully encircle the guide plate 10. Each anchor body 21/22 is provided with an internally threaded bore 25 that is sized and configured to receive a threaded portion 51/52 of the force adjusting rod 50, whereby rotation of the force adjusting rod 50 results in axial movement of the anchor bodies 21/22 along the force adjusting rod member 50 and the guide plate 10. The anchor bodies 21/22 are free sliding along the guide plate 10.

The force adjusting rod member 50 comprises a first threaded portion 51 and a second threaded portion 52 threaded oppositely from the first threaded portion, i.e., one of the threaded portions 51/52 is a left-handed thread and the other is a right-handed thread. The central portion 54 of the force adjusting rod 50 is preferably non-threaded. The first anchor body 21 is disposed on the first threaded portion 51 and the second anchor body 22 is disposed on the second threaded portion 52. One end of the force adjusting rod 50 is structured as a drive end 53 possessing a shape that mates with a drive tool, such as for example a hex socket screwdriver or the like. Alternatively, the drive end 53 could be provided with a shape and surface structure that enables rotation of the force adjusting tool 50 by hand.

The distraction device is preferably provided with a central hub member 60 possessing a non-threaded bore 61 adapted and structured to receive the central portion 54 of the force adjusting rod 50 there through, such that the central hub member 60 does not mechanically engage with any threaded portion of the force adjusting rod 50. The central guide hub member 60 is joined to the central portion of the guide plate 10. With this structure, the first distractor body 31 and the first anchor body 21 are positioned to one side of the central hub member 60 and the second distractor body 32 and the second anchor body 22 are positioned to the other side of the central hub member 60.

First and second helical distraction springs 41/42 are coaxially disposed on the force adjusting rod 50. The first distraction spring 41 is affixed to and connects both the first distraction body 31 and the first anchor body 21. The second distraction spring 42 is affixed to and connects both the second distraction body 32 and the second anchor body 22. When the distraction springs 41/42 are extended, separation force is applied to the distraction bodies 31/32, respectively.

FIG. 1 illustrates the distractor in the initial, non-tensioned, pre-adjustment state, the distractor bodies 31/32 being generally centrally positioned on the force adjustment rod 50 and the guide plate 10 adjacent the central hub member 60. The anchor bodies 21/22 are disposed toward the center of the force adjusting rod 50 such that distraction springs 41/42 are fully compressed and no tension is placed on the distractor bodies 31/32. With the distractor in this neutral state, the bone abutting members 33 of the distractor bodies 31/32 are inserted into the craniotomy opening and positioned such that each bone abutting member 33 faces or abuts the exposed edges of the cranial bones to be distracted.

Figure 2:
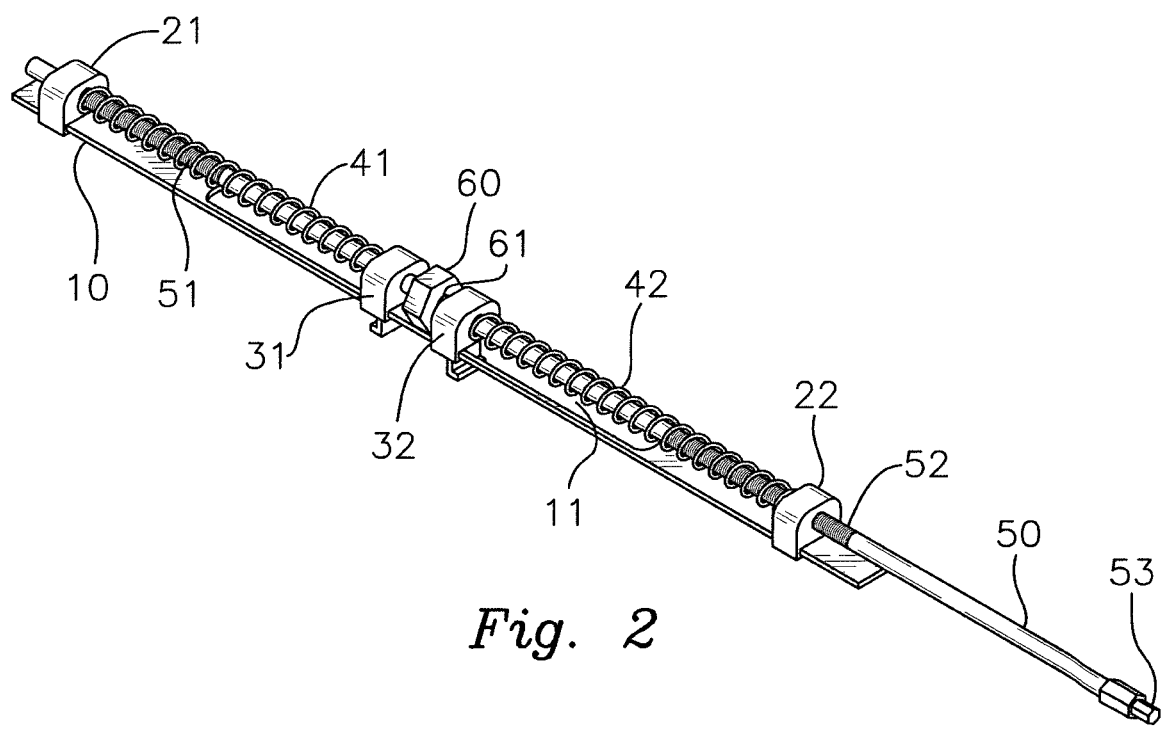
FIG. 2 is a perspective view of the distractor of FIG. 1 shown in the tensioned state, after the separation force of the distractor has been adjusted.
Figure 3:
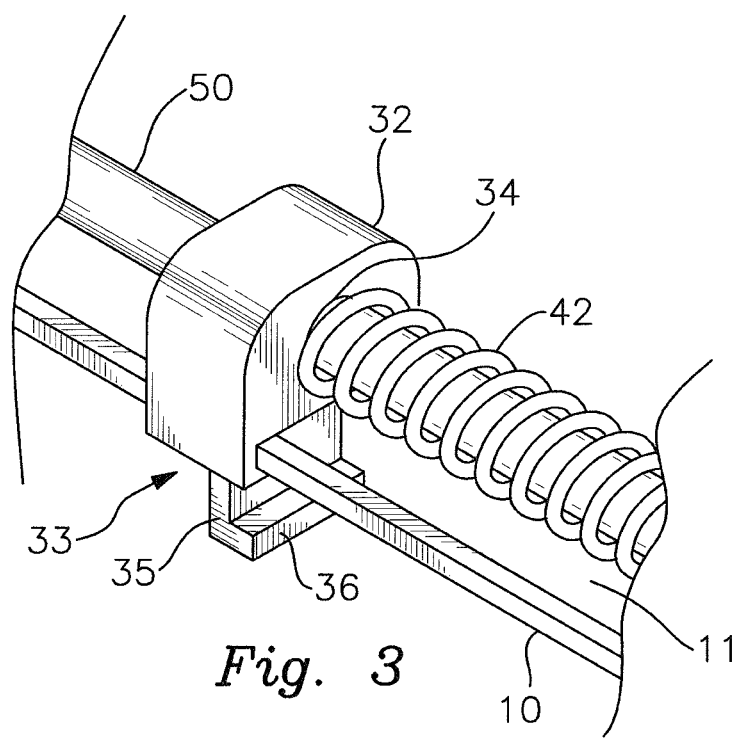
FIG. 3 is a perspective view showing one of the bone distractor members of the distraction device of FIG. 1.
Figure 4:
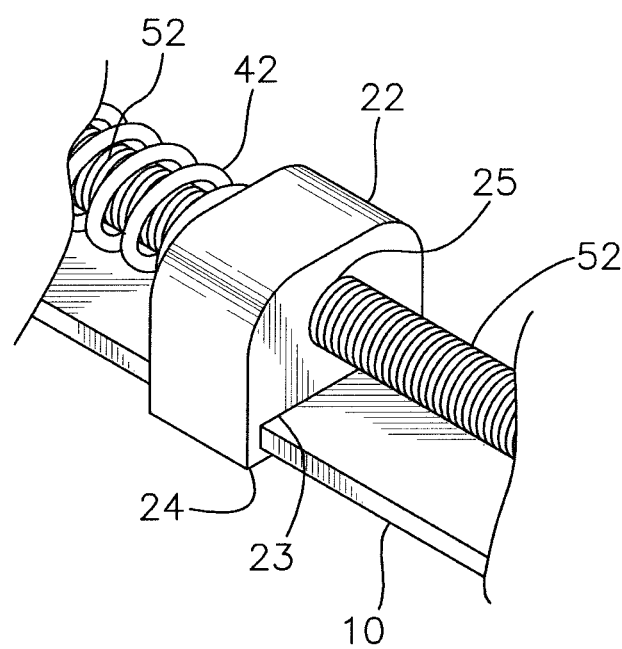
FIG. 4 is a perspective view showing one of the anchor members of the distraction device of FIG. 1.

Force adjusting rod 50 is then rotated in a first direction. Because the first threaded portion 51 of the force adjusting rod 50 associated with the first anchor body 21 is oppositely threaded relative to the second threaded portion 52 of the force adjusting rod associated with the second anchor body 22, rotation of the force adjustment rod 50 results in separation of the anchor bodies 21/22 from each other in the axial direction, which in turn elongates the distraction springs 41/42, as shown in FIG. 2. This action first tightens or snugs the bone distracting bodies 31/32 against the cranial bone members and then applies an increasing distraction force to the distractor bodies 31/32, which is directly transferred to the cranial bone members. Once the desired amount of distraction force is reached, typically between about 6 to 8.5 Newtons, rotation of the force adjusting rod 50 is stopped. Due to the continuous application of force imparted by the distraction springs 41/42 against the cranial bones, the bones will gradually separate and the distractor bodies 31/32 will move outwardly toward the anchor bodies 21/22, respectively. As the distraction springs 41/42 compress, the force applied to the distractor bodies 31/32 will diminish. Thus, after a given period of time it will be necessary to further separate the anchor bodies 21/22 by rotating the force adjusting rod 50 in order to elongate the distraction springs 41/42 to maintain the desired separation force. Alternatively, conditions may arise wherein the separation force needs to be reduced, such as if the initial force is damaging the cranial bones, in which case the force adjusting rod 50 is rotated in the opposite direction so as to move the anchor bodies 21/22 together to shorten the distraction springs 41/42.

Figure 5:
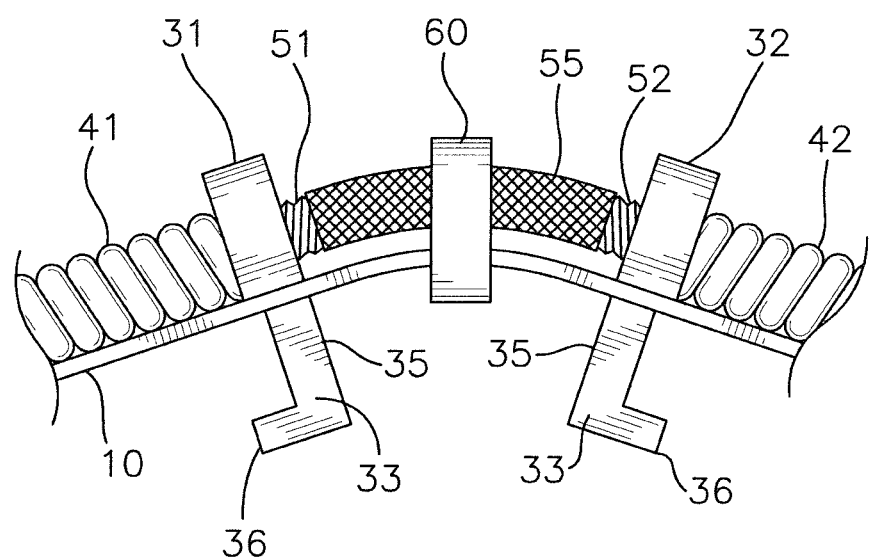
FIG. 5 is a partial view of an alternative embodiment of the distractor showing a force adjustment rod member with an axially flexible central portion.

In an alternative embodiment as shown in FIG. 5, the central portion 54 of the force adjusting rod 50 may be structured as an axially flexible, i.e., flexible from a linear configuration to a non-linear configuration, central portion 55 composed of a cable or similar structure having sufficient torsional rigidity to maintain the ability to transmit rotational force from the drive end 53 to the opposite end of the force adjusting rod member 50. This structure allows the middle portion of the guide plate 10 to be non-linear, i.e., curved, angled or hinged, so as to better accommodate the rounded shape of the cranium. In other embodiments, the distraction springs 41/42 may be provided with a flexible sleeve or cover, or the bone abutting members 33 may be turned in the opposite direction such that the device could also be used for contraction to force two cranial bones together. Furthermore, the device is not limited to application to cranial bones, but could also be utilized with long bones, mandibles, etc. The device may be implanted beneath the skin with only the drive end 53 of the force adjusting rod 50 exposed, or it may be externally mounted. The strength of the distraction springs 41/42 and the pitch of the threaded portions 51/52 may vary and will be chosen depending on patient factors.

It is contemplated and understood that equivalents and substitutions for certain elements set forth above may be obvious to those of skill in the art, and therefore the true scope and definition of the invention is to be as set forth in the following claims.

We claim:
1. A force adjustable bone distractor comprising:
a threaded force adjusting rod member, said force adjusting rod member having a first threaded portion and a second threaded portion wherein the threading of said first threaded portion is opposite from the threading of said second threaded portion, said force adjusting rod member defining an axial direction;
an elongated guide plate connected to said force adjusting rod member;
a first distractor body and a second distractor body each positioned on said force adjusting rod member, wherein said first and second distractor bodies are free sliding along said force adjusting rod member and along said guide plate;
a first anchor body and a second anchor body, each of said first and second anchor bodies having a threaded bore, wherein the threaded bore of said first anchor body engages said first threaded portion of said force adjusting rod member and the threaded bore of said second anchor body engages said second threaded portion of said force adjusting rod member, and wherein said first and second anchor bodies are free sliding along said guide plate;
a helical first distraction spring coaxially positioned on said first threaded portion of said force adjusting rod member and a helical second distraction spring coaxially positioned on said second threaded portion of said force adjusting rod member, said first distraction spring connecting said first distractor body with said first anchor body, said second distraction spring connecting said second distractor body with said second anchor body; and
wherein rotation of said force adjusting rod member separates said first anchor body from said second anchor body such that said first distraction spring applies force to said first distractor body and said second distraction spring applies force to said second distractor body.

2. The distractor of claim 1, further comprising a central hub member, said central hub member connecting said force adjustable rod member to said guide plate.

3. The distractor of claim 2, said central hub member comprising a non-threaded bore adapted to receive said force adjusting rod member there through.

4. The distractor of claim 1, said guide plate further comprising one or more slots, wherein said first and second distractor bodies extend through said one or more slots, said slots allowing for movement of said first and second distractor bodies in the axial direction while restricting movement in non-axial directions.

5. The distractor of claim 1, said first distractor body and said second distractor body each comprising a bone abutting member, each said bone abutting member comprising a leg portion and a foot portion.

6. The distractor of claim 4, said first distractor body and said second distractor body each comprising a bone abutting member, each said bone abutting member comprising a leg portion extending through said one or more slots and a foot portion.

7. The distractor of claim 1, said first anchor body and said second anchor body each comprising a mounting slot adapted to receive said guide plate there through.

8. The distractor of claim 5, said first anchor body and said second anchor body each comprising a mounting slot adapted to receive said guide plate there through.

9. The distractor of claim 6, said first anchor body and said second anchor body each comprising a mounting slot adapted to receive said guide plate there through.

10. The distractor of claim 1, said force adjusting rod member further comprising an axially flexible central portion.

11. The distractor of claim 10, wherein the middle portion of said guide plate is curved in the axial direction.

12. A force adjustable bone distractor comprising:
an externally threaded, elongated, force adjusting rod member, said force adjusting rod member having a first threaded portion and a second threaded portion wherein the threading of one of said first or second threaded portions is right handed and the threading of the other of said first or second threaded portions is left handed, said force adjusting rod member having a central axis defining an axial direction;
an elongated guide plate connected to said force adjusting rod member by a central hub member, wherein said force adjusting rod member extends through said central hub member;
a first distractor body and a second distractor body each positioned on said force adjusting rod member on opposite sides of said central hub member, wherein said first and second distractor bodies are free sliding in the axial direction along said force adjusting rod member and along said guide plate;
a first anchor body and a second anchor body each positioned on said force adjusting rod member on opposite sides of said central hub member, each of said first and second anchor bodies having a threaded bore, wherein the threaded bore of said first anchor body engages said first threaded portion of said force adjusting rod member and the threaded bore of said second anchor body engages said second threaded portion of said force adjusting rod member, such that rotation of said force adjusting rod member separates said first and second anchor members in the axial direction, and wherein said first and second anchor bodies are free sliding along said guide plate;
a helical first distraction spring coaxially positioned on said first threaded portion of said force adjusting rod member and a helical second distraction spring coaxially positioned on said second threaded portion of said force adjusting rod member, said first distraction spring connecting said first distractor body and said first anchor body, said second distraction spring connecting said second distractor body and said second anchor body; and
wherein said first distraction spring applies force to said first distractor body in the axial direction and said second distraction spring applies force to said second distractor body in the axial direction upon separation of said first anchor body from said second anchor body by rotation of said force adjusting rod member.

13. The distractor of claim 12, said guide plate further comprising one or more slots, wherein said first and second distractor bodies extend through said one or more slots, said slots allowing for movement of said first and second distractor bodies in the axial direction while restricting movement in non-axial directions.

14. The distractor of claim 12, said first distractor body and said second distractor body each comprising a bone abutting member, each said bone abutting member comprising a leg portion and a foot portion.

15. The distractor of claim 13, said first distractor body and said second distractor body each comprising a bone abutting member, each said bone abutting member comprising a leg portion extending through said one or more slots and a foot portion.

16. The distractor of claim 12, said first anchor body and said second anchor body each comprising a mounting slot adapted to receive said guide plate there through.

17. The distractor of claim 14, said first anchor body and said second anchor body each comprising a mounting slot adapted to receive said guide plate there through.

18. The distractor of claim 15, said first anchor body and said second anchor body each comprising a mounting slot adapted to receive said guide plate there through.

19. The distractor of claim 12, said force adjusting rod member further comprising an axially flexible central portion.

20. The distractor of claim 19, wherein the middle portion of said guide plate is curved in the axial direction.

* * * * *